(12) United States Patent
Sanford

(10) Patent No.: US 10,019,553 B2
(45) Date of Patent: Jul. 10, 2018

(54) SYSTEMS AND METHODS FOR VIRTUALLY INTEGRATED CARE DELIVERY

(71) Applicant: Catholic Health Initiatives, Englewood, CO (US)

(72) Inventor: Kathleen D. Sanford, Olalla, WA (US)

(73) Assignee: Catholic Health Initiatives, Englewood, CO (US)

( * ) Notice: Subject to any disclaimer, the term of this patent is extended or adjusted under 35 U.S.C. 154(b) by 0 days.

(21) Appl. No.: 15/007,926

(22) Filed: Jan. 27, 2016

(65) Prior Publication Data

US 2016/0217264 A1    Jul. 28, 2016

Related U.S. Application Data

(60) Provisional application No. 62/108,257, filed on Jan. 27, 2015.

(51) Int. Cl.
| | |
|---|---|
| H04N 7/15 | (2006.01) |
| G06F 19/00 | (2018.01) |
| H04N 7/14 | (2006.01) |
| H04L 12/18 | (2006.01) |

(52) U.S. Cl.
CPC ...... *G06F 19/3418* (2013.01); *H04L 12/1822* (2013.01); *H04N 7/147* (2013.01)

(58) Field of Classification Search
CPC ........ G06Q 50/22; G06Q 50/24; G06F 19/30; G06F 19/32; G06F 19/321; G06F 19/322; G06F 19/323; G06F 19/324; G06F 19/325; G06F 19/326; G06F 19/327; G06F 19/34; G06F 19/3406; G06F 19/3418; G06F 19/3425; H04N 7/152
See application file for complete search history.

(56) References Cited

U.S. PATENT DOCUMENTS

| | | | |
|---|---|---|---|
| 2004/0125938 A1* | 7/2004 | Turcan | H04M 3/42323 379/265.02 |
| 2007/0016442 A1* | 1/2007 | Stroup | G06Q 50/22 705/2 |
| 2011/0214153 A1* | 9/2011 | Rosenfeld | H04N 7/15 725/78 |

(Continued)

*Primary Examiner* — Stella Woo
(74) *Attorney, Agent, or Firm* — Polsinelli PC

(57) ABSTRACT

Disclosed herein are systems and methods for virtually integrated care delivery. In one implementation, a provider controller is disposed in a virtual care command center and has a provider care delivery interface. Patient controllers and provider user devices are in communication with the provider controller over a network and are each associated with a patient room and have a patient care delivery interface. The provider controller obtains real-time video from the patient controllers for presentation using the provider care delivery interface. The real-time video is captured using the patient care delivery interfaces and provides real-time surveillance of the patient rooms in the virtual care command center. A communication manager device is deployed in the network and configured to route communications among the controllers and user devices and routes a round coordination communication from the provider controller to a subset of the provider user devices associated with providers for a patient.

8 Claims, 13 Drawing Sheets

(56) References Cited

U.S. PATENT DOCUMENTS

| | | | |
|---|---|---|---|
| 2011/0307284 A1* | 12/2011 | Thompson | G06F 19/327 705/7.13 |
| 2012/0120184 A1* | 5/2012 | Fornell | H04N 7/15 348/14.12 |
| 2012/0278104 A1* | 11/2012 | Traughber | G08B 5/222 705/3 |
| 2013/0147899 A1* | 6/2013 | Labhard | G06F 19/3418 348/14.03 |
| 2013/0218583 A1* | 8/2013 | Marcolongo | G06F 19/327 705/2 |
| 2014/0118468 A1* | 5/2014 | Purdy | H04N 7/141 348/14.08 |
| 2014/0267582 A1* | 9/2014 | Beutter | H04N 7/147 348/14.12 |
| 2015/0019234 A1* | 1/2015 | Cooper | G06Q 10/06393 705/2 |
| 2015/0049164 A1* | 2/2015 | Krishnamoorthy | H04N 7/147 348/14.11 |
| 2016/0027289 A1* | 1/2016 | Hargis | G08B 25/016 340/286.07 |

* cited by examiner

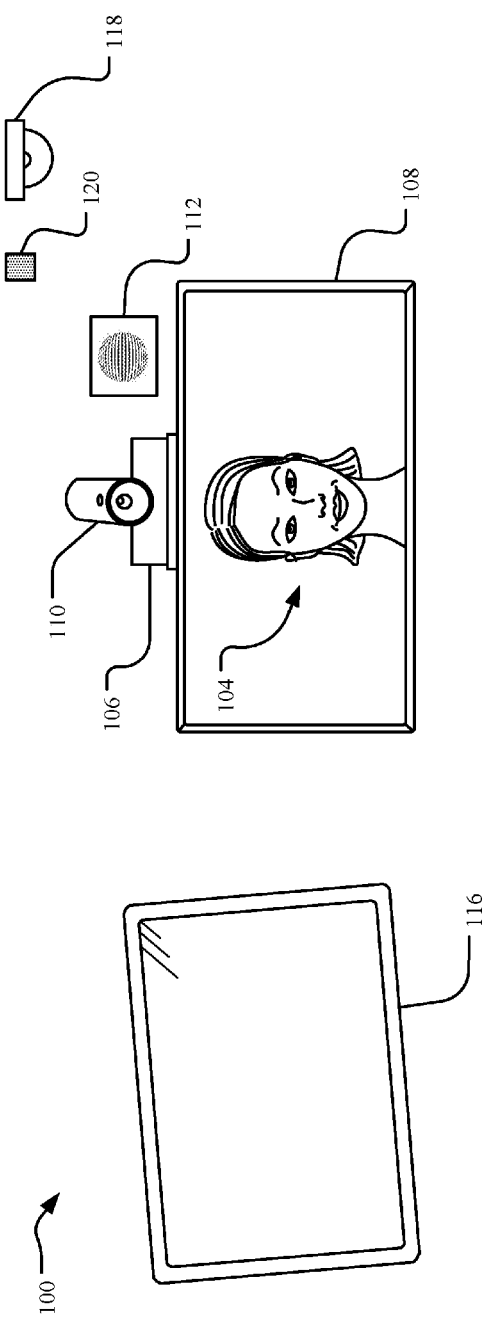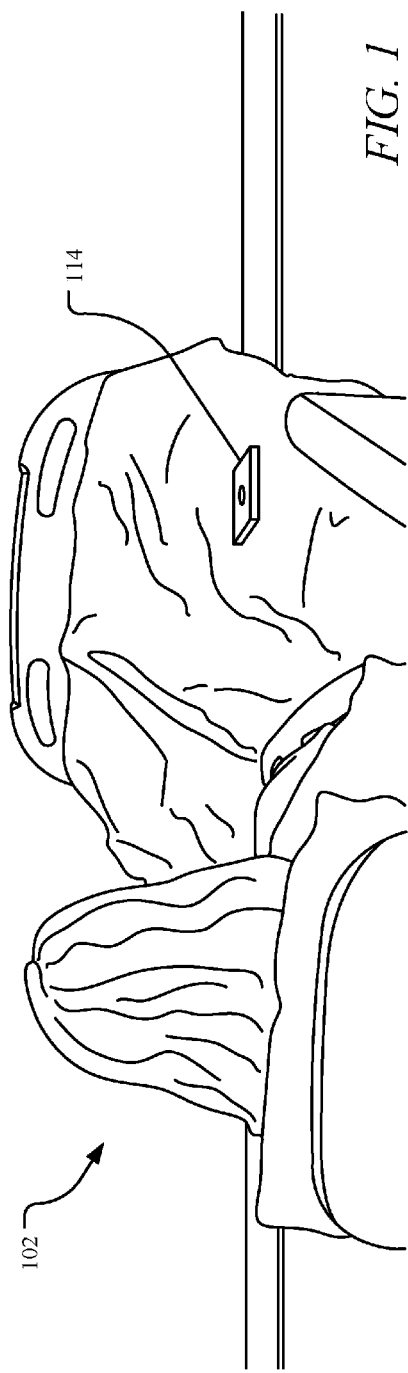
FIG. 1

SYSTEMS AND METHODS FOR VIRTUALLY INTEGRATED CARE DELIVERY

CROSS-REFERENCE TO RELATED APPLICATIONS

The present application claims benefit under 35 U.S.C. § 119 to U.S Provisional Patent Application No. 62/108,257, entitled "Systems and Methods for Virtually Integrated Care Delivery" and filed on Jan. 27, 2015, which is specifically incorporated herein in its entirety.

TECHNICAL FIELD

Aspects of the present disclosure relate to patient management and healthcare delivery and more particularly to systems and methods for virtually integrated care delivery.

BACKGROUND

Current trends at the national level in the United States, including the aging of the general population and the impact of the passage of the Affordable Care Act, are driving significant changes across all healthcare venues. Conventional models of care delivery emphasize hospitals as central to healthcare. Unfortunately, due to the nature of hospital systems under conventional models, there is often a large variance in treatments, prescriptions, and outcomes, and customer service is not a priority. Thus, under the current trends in the hospital setting, increased complexity and acuity of patient needs coupled with shorter stays and higher patient expectations result in a significant demand for reconfiguration of bedside care delivery to advance coordination of care. However, an ongoing shortage of highly trained nurses and other medical professionals, new and challenging financial incentive models, and inefficient conventional staffing models represent significant practical difficulties in initiating positive change.

A shortage of medical professionals remains an ongoing problem in care delivery in the United States. Changing demographics, both in terms of the expansion of the number of aged patients with complex needs and the aging of the experience nursing workforce, contributes to a disturbing nursing shortage in the United States, with the shortage of advanced practice and nurse leaders even more severe. Currently, the United States healthcare system is short over 40,000 nurses and 63,000 physicians with even greater shortages on the horizon if this trend continues. By 2020, there will be a shortage of 91,500 physicians and 340,000 nurses. These shortage trends result in increased staff stress due to insufficient coverage and extended overtime hours. Many hospital nurses report an erosion of the collaborative relationship with other care team members as well as major barrier to the quality of patient care through their compromised ability to detect, prevent, and/or address complications in a timely manner.

Additionally, a majority of patients encounter various challenges in accessing and receiving healthcare. Approximately 56 million Americans live in rural areas with inadequate access to primary healthcare. Of those that have access to healthcare, approximately 33% of patients reported problems in accessing and receiving care from their primary care physician, and approximately 73% of patients have difficulty making timely appointments, receiving phone advice, or receiving after-hours care. Further exacerbating these challenges, many physician office and emergency room visits are unnecessary. There are 120 million emergency room visits per year, with approximately 64% being non-emergency visits requiring only basic medical services. The total cost per year of unnecessary physician office and emergency room visits is nearly 31 billion dollars. Under the current model of healthcare delivery, this amount will only continue to grow with an expected 31 million additional patients in the United States by the end of 2014.

A healthcare delivery model is needed that addresses patient care quality issues, inpatient coordination issues, interdisciplinary relationships and communication issues, shortages of healthcare professionals, rising healthcare costs, continuum and coordination of care issues, 30 day readmissions, inpatient chaos, and the like. It is with these observations in mind, among others, that various aspects of the present disclosure were conceived and developed.

SUMMARY

Implementations described and claimed herein address the foregoing problems by providing systems and methods for virtually integrated care delivery. In one implementation, a provider controller is disposed in a virtual care command center. The provider controller has a provider care delivery interface. A plurality of patient controllers is in communication with the provider controller over a network. Each of the plurality of patient controllers is associated with a patient room and have a patient care delivery interface. The provider controller obtains real-time video from each of the patient controllers over the network for presentation using the provider care delivery interface. The real-time video is captured using the patient care delivery interfaces and provides real-time surveillance of the patient rooms in the virtual care command center. A plurality of provider user devices is in communication with the provider controller over the network. At least one communication manager device is deployed in the network. The at least one communication manager device is configured to route communications among the provider controller, the plurality of patient controllers, and the plurality of provider user devices. The at least one communication manager device routes a round coordination communication from the provider controller to a subset of the plurality of provider user devices. The subset of the plurality of provider user devices is associated with providers for a patient.

In another implementation, a care delivery communication is received from a provider controller disposed in a virtual command center. The care delivery communication is initiated through a selection of a patient room from a directory of patient rooms using the provider controller. The care delivery communication is routed over a network to a patient controller associated with the patient room using at least one communication manager device. The care delivery communication is delivered to the patient controller as an audio exclusive connection between the patient controller and the provider controller. The audio exclusive connection includes a request for a care visit session. Upon acceptance of the request for the care visit session, a video connection between the patient controller and the provider controller is delivered to initiate the care visit session.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 1 illustrates an example system for providing virtually integrated care delivery for a patient.

DETAILED DESCRIPTION

Figure 2:
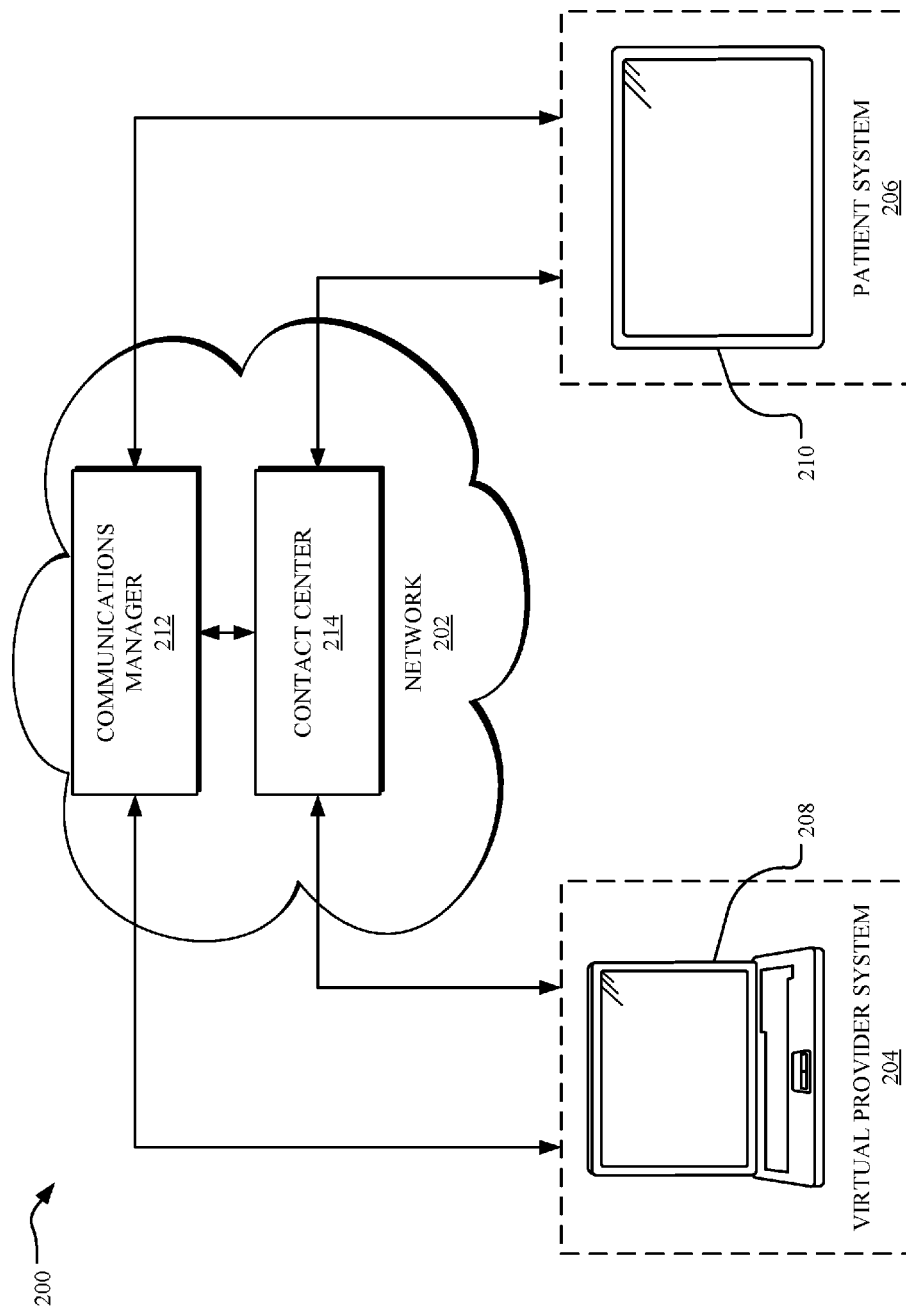
FIG. 2 shows an example network environment for monitoring and communicating with one or more patients during care delivery.

Aspects of the present disclosure involve systems and methods for virtually integrated care delivery. Generally, the virtually integrated care delivery provides a care model that enhances the collaborative practice environment in the acute care setting. Advanced care nurses coordinate care delivery for patients by leveraging information and communication services to streamline workflows, promoting effective discourse, and integrating real-time patient monitoring and management. In one particular aspect, the advanced care nurse directs the care of one or more patients remotely, in partnership with an interprofessional care team, over a network. The advanced care nurse may connect to patient rooms from a virtual command center through videoconferencing to support efficient, effective patient-centered care and education while also providing a virtual support system for care team members. The virtually integrated care delivery system provides real-time surveillance of patient rooms, facilitates admission and discharge activities, facilitates physician rounding through round coordination communications, provides staff mentoring and education, and provides patient education and resources.

The interprofessional team may include any number of medical professionals or other authorized personnel, including, without limitation, advanced care nurses, unit-based registered nurses, licensed practical nurses, certified nursing assistants, hospitalists, specialty physicians, social workers, case managers who coordinate patient care, primary physicians, other caregivers, patients, family members, and the like. Communication among the interprofessional team confirms all members of the team are well informed regarding patient needs and provides the best possible outcomes during and after a hospital stay. By providing additional support and emphasizing patient-centered care, quality of care is increased and a collaborative practice environment is promoted through the integration of nurse leadership roles while leveraging information and communication technologies. As such, aspects of the present disclosure address current shortages in nursing leadership and make the most efficient use of current limited resources, while achieving additional efficiencies in care and education availability, establishing a collaborative relationship between the patient and the care providers, and facilitating coordinated interactions among the members of the interprofessional team.

To begin a detailed description of an example system 100 for providing virtually integrated care delivery for a patient 102, reference is made to FIG. 1. In one implementation, a virtual nurse 104 interacts with the patient 102 via a patient controller 106 using a patient care delivery interface associated with a room for the patient 102. The patient care delivery interface is in communication with the patient controller 106 and may include one or more various interface devices, including, without limitation, one or more cameras, one or more displays, one or more microphones, one or more speakers, one or more user devices, and other input or output devices. It will be appreciated that such features may be provided as one device or multiple devices in communication. For example, in one particular implementation, the patient care delivery interface includes a display 108, a day camera 110 configured to capture one or more images, image sequences, and/or videos using ambient light in daytime lighting conditions while the sun is up, a patient user device 114, a microphone 112, an auxiliary display 116, a night-vision camera 118 configured to capture one or more images, image sequences, and/or videos using ambient light in nighttime lighting conditions while the sun is down, and/or a speaker 120. The patient user device 114 may be, for example, a touch-screen display (e.g., a tablet or touch-screen monitor) or any other form of computing device, such as a personal computer, terminal, smartphone, multimedia console, remote control, and/or the like.

The patient 102 is provided with the patient user device 114, which has a call button to access the virtual nurse 104 or other health professional or information. In one implementation, the patient user device 114 is a remote control having a physical button, which when depressed, sends a signal to the patient controller 106 to initiate a call to the virtual nurse 104. In another implementation, the patient user device 114 is a tablet or touch-screen monitor, as described in more detail with respect to FIG. 13, which displays a graphical call button that when selected causes the patient user device 114 to call the virtual nurse 104 either directly or via the patient controller 106.

In one implementation, the patient controller 106 is a computing device configured to provide telecommunication services, including video and/or voice calls, multimedia messaging, file and image exchange, and/or the like. The virtual nurse 104 may be an advanced care nurse or other highly trained medical professional that directs the care of the patient 102 remotely in partnership with other healthcare providers and utilizing various data sources, including patient diagnostic records, and integrated medical devices. In some implementations, at least some of the functions performed by the virtual nurse 104 may be automated with an avatar displayed on the display 108 to the patient 102.

The admission and discharge of the patient 102 may be complex and time consuming for a bedside nurse already challenged with multiple tasks and priorities. However, a complete assessment upon admission of the patient 102 ensures attention to unique needs of the patient 102 during the hospital stay. Accordingly, in one implementation, the virtual nurse 104 engages with the patient 102 using the patient controller 106 at the time of admission for assessment of the needs of the patient 102. The virtual nurse 104 may video conference with the patient 102, such that an image of the virtual nurse 104 is presented on the display 108, with the camera 110 and the microphone 112 permitting the patient 102 to communicate with the virtual nurse 104. In some implementations, at least a portion of the admission process may be automated with the virtual nurse 104 being generated by the patient controller 106 and the admission information of the patient 102 captured using the camera 110, the microphone 112, the patient user device 114, and/or other input devices.

Similarly, the discharge process is often multilayered, necessitating attention to multiple details regarding continuing care, physician follow up, medication management, and patient wellbeing upon discharge. Delays in discharges are frequent, particularly where specific elements of a discharge plan are missing, incomplete, or ambiguous, thereby often contributing to unnecessary readmissions. The system 100 facilitates planning for discharge throughout the hospital stay, such that all elements of a complete and effective discharge plan are in place for discharge once approved by the admitting physician. In one implementation, the virtual nurse 104, the patient controller 106, and/or other computing device in communication with the patient controller 106 tracks patient assessments for the patient 102, including, without limitation, demographic, fall risks, nutrition screening, medication management/reconciliation, spiritual assessment, risk for embolism, and the like, in preparation for discharge. The virtual nurse 104, the patient controller 106, and/or another computing device may automatically and/or manually generate and update a discharge plan for the patient 102 based on the tracked patient assessments. Utilization of the virtual nurse 104 therefore improves discharge procedures addressing risks for patient care and readmissions, while improving patient and medical professional satisfaction and increasing confidence in the transition out of the hospital.

Many patients fail to understand the nature of their medical conditions or appreciate the necessity of following medical professionals' instructions upon discharge. Accordingly, the system 100 provides proactive education for the patient 102 about the medical condition, the care delivery plan during the hospital stay, the discharge plan, including medications the patient 102 should take and instructions to follow. In some implementations, the patient 102 may use the patient controller 106 to access additional information. For example, the patient 102 may call the virtual nurse 104 to ask a question or use the patient controller 106 to generate a query, to which an answer is automatically generated, as described herein. Furthermore, in some implementations, the patient 102 may access information, including the discharge plan, from home or otherwise remotely using a healthcare portal, as described herein. The virtual nurse 104 thus provides mentoring and support for patients with complex diagnoses or multiple comorbidities.

In one implementation, the virtual nurse 104 critically evaluates and anticipates risks for the patient 102. The virtual nurse 104 provides real-time monitoring and risk analysis, including, without limitation, real-time patient room surveillance, alerts, patient data capture and tracking, and/or the like. Clinical decision support tools, patient data, and clinical quality indicators may be used by the virtual nurse 104 to generate or otherwise provide real-time early warning surveillance alerts for the patient 102 to one or more members of the interprofessional team. The integration of real-time monitoring of the patient 102 contributes to improved clinical quality and completeness of care (e.g., avoidance of adverse events, etc.) and future reductions in length of stay and readmission rates. The virtual nurse 104 may further proactively monitor unit performance measures and suggested course corrections to implement preventative measures for recurring issues and/or performance improvements for increased accountability and quality of care.

The presently disclosed technology thus provides systems and methods for virtually integrated care delivery. In one implementation, a virtual care delivery model combines monitoring and communication services with a remodeling of nursing roles to provide an efficient and effective healthcare delivery system that enhances patient satisfaction and quality of care. The model includes a clinical nurse leader that directs the care of the patient remotely in partnership with other healthcare providers and utilizing various data sources, including patient diagnostic records, and integrated medical devices. The clinical nurse leader communicates with the patient and other medical providers over a network to provide care delivery.

Turning to FIG. 2, an example network environment 200 for monitoring and communicating with one or more patients during care delivery is shown. In one implementation, a virtual provider system 204 of a virtual command center is in communication with one or more patient systems 206 over a network 202 (e.g., the Internet, an intranet, a Virtual Private Network (VPN), Voice over Internet Protocol (VoIP), etc.) to improve productivity and increase the use of a care team's time on the unit for one or more patients.

In one implementation, the virtual provider system 204 and the patient systems 206 each include a communication device 208 and 210, respectively, for communicating over the network 202. The communication devices 208, 210 may be generally any form of computing device capable of interacting with the network 202, such as a controller, a personal computer, terminal, workstation, portable computer, mobile device, tablet, phone, pager, multimedia console, or other Internet Protocol (IP)-based telecommunication devices.

The virtual provider system 204, the patient systems 206, and communication devices used by other members of the interprofessional team may be in communication with a communications manager device 212 and a contact center 214 over the network 202. In one implementation, the communication device 208 disposed in the virtual command center or otherwise included in the virtual provider system 204 is a provider controller having a provider care delivery interface, which may include one or more cameras, microphones, speakers, and/or displays. The communication device 208 of the virtual provider system 204 is in communication with the communication devices 210 of the one or more patient systems 206 over the network 202. In one implementation, each of the communication devices 210 is a patient controller associated with a patient room. The communication device 210 includes a patient care delivery interface, which may include one or more cameras (e.g., a day camera, a night-vision camera, etc.), microphones, speakers, and/or displays (e.g., a touch-screen display, etc.). A plurality of provider user devices, each associated with a provider, may further be in communication with the communication device 208 of the virtual provider system 204 and/or the communication devices 210 of the patient systems 206 over the network 202. The provider user devices may be, without limitation, a controller, a personal computer, terminal, workstation, portable computer, mobile device, tablet, phone, pager, multimedia console, or other IP-based telecommunication devices.

In one implementation, the communication device 208 in the virtual provider system 204 obtains real-time video from each of the communication devices 210 of the patient systems 206 over the network 202 for presentation using the provider care delivery interface. The real-time video is captured using the patient care delivery interfaces associated with the communication devices 210. The real-time video provides real-time surveillance of the patient rooms in the virtual command center with the virtual provider system 204.

In one implementation, the communications manager device 212 utilizes Session Initiation Protocol (SIP) to route communications (e.g., video, audio, multimedia, text, or other content communications) within the network 202 to the appropriate party, such as providers (e.g., to the provider user devices), the virtual command center (e.g., to the communication device 208), and the patients (e.g., the communication devices 210). The communications manager device 212 integrates inbound and outbound voice applications with Internet applications to provide various communication services, including real-time conferencing, collaborating, and messaging, while supporting multiple interactions simultaneously independent of the communications channel. In one implementation, a round coordination communication from the communication device 208 is routed by the communications manager device 212 to a subset of the provider user devices that are associated with providers for a patient. Similarly, the communications manage device 212 may route requests for care visit sessions between the virtual provider system 204 and particular patient systems 206, as appropriate.

The contact center 214 may be configured to maintain a call queue of communications for acceptance by the communication device 208 of the virtual provider system 204. The contact center 214 may maintain the communications according to an assigned priority. For example, the patient 102 or a provider may indicate in initiating the communication whether there is an elevated priority. The contact center 214 may further distinguish patient initiated communications from provider initiated communications within the call queue, for example, based on an identification of the device from which the communication originated (e.g., using the IP address of the device) or through input captured using the device.

The virtual provider system 204 may be used to coordinate the admission and discharge process, provide real-time surveillance, provide mentoring and education, facilitate physician rounding, facilitate communication with members of the interprofessional team, and the like over the network 202. For example, the care delivery interfaces associated with the communication devices 208 and 210 may be used to capture patient admission information and provide patient discharge information. Further, the communication device 208 may be used to send shared medical content to one of the communication devices 210 for presentation using a respective patient care delivery interface. This information may be stored in one or more databases in communication with the communication device 208 over the network 202.

In one implementation, the virtual provider system 204 conducts rounds with unit staff (shift rounding) as well as with hospitalists, specialty physicians, social workers, case managers, and other members of the interprofessional team as necessary. Conventional care delivery models suffer from disconnects during rounds where a unit nurse or other professional cannot be located to make rounds or orders are not removed or revised in a timely manner, thereby delaying appropriate treatment or care. As such, the virtual provider system 204 contacts the appropriate team members using a round coordination communication to improve rounding and effectively integrate the patient into the conversation about their care and identify patient needs and education support.

Management of patient call light responses is crucial to ensuring the right staff member responds to the patient in a timely manner. Work on units may be chaotic with multiple pages interrupting patient care or other important tasks. Critical alerts may be missed if the queue is long, and alert fatigue in nurses or other medical professionals may compromise the wellbeing of patients. Accordingly, the virtual provider system 204 decreases the initial response times and matches the tasks to the correct team member(s) through on-demand patient call and care coordination. In one implementation, the contact center 214 receives a call from the patient system 206 and places the call in a queue. The call may be placed in the queue according to a priority or urgency of the call. The virtual provider system 204 then analyzes the nature of the call and matches the call to the appropriate team member(s), who are then notified using the communications manager device 212 and dispatched for response. The virtual provider system 204 thus improves nursing and team member performance and patient outcomes while improving patient satisfaction with care and timeliness of response.

In one implementation, the virtual provider system 204 provides proactive staff education and mentoring to facilitate oversight and assistance for unit nursing staff members who are less experienced or facing uncommon patient conditions or complex comorbidities. Furthermore, the virtual provider system 204 may provide routine continuing education and training to ensure the staff is consistently implementing best and current practices. In one implementation, the virtual provider system 204 may track performance issues and provide suggested improvements to address recurring or new issues.

As a result, the network environment 200 provides a patient-centered care delivery, with care extending beyond hospital settings to offices, clinics, neighborhood centers, long term care facilities, and the patient home. The network environment 200 emphasizes customer service and quality of care as priorities and reduces variance in care in treatments, prescriptions and outcomes. The network environment provides effective interprofessional collaboration through increased communication and shared decision-making among practitioners, virtual rounding, and integration of staff education and mentoring. Furthermore, a mutual respect and effective dialogue among team members flow from the network environment 200 through care coordination, proactive planning, and real-time problem solving and accountability.

Figure 3:
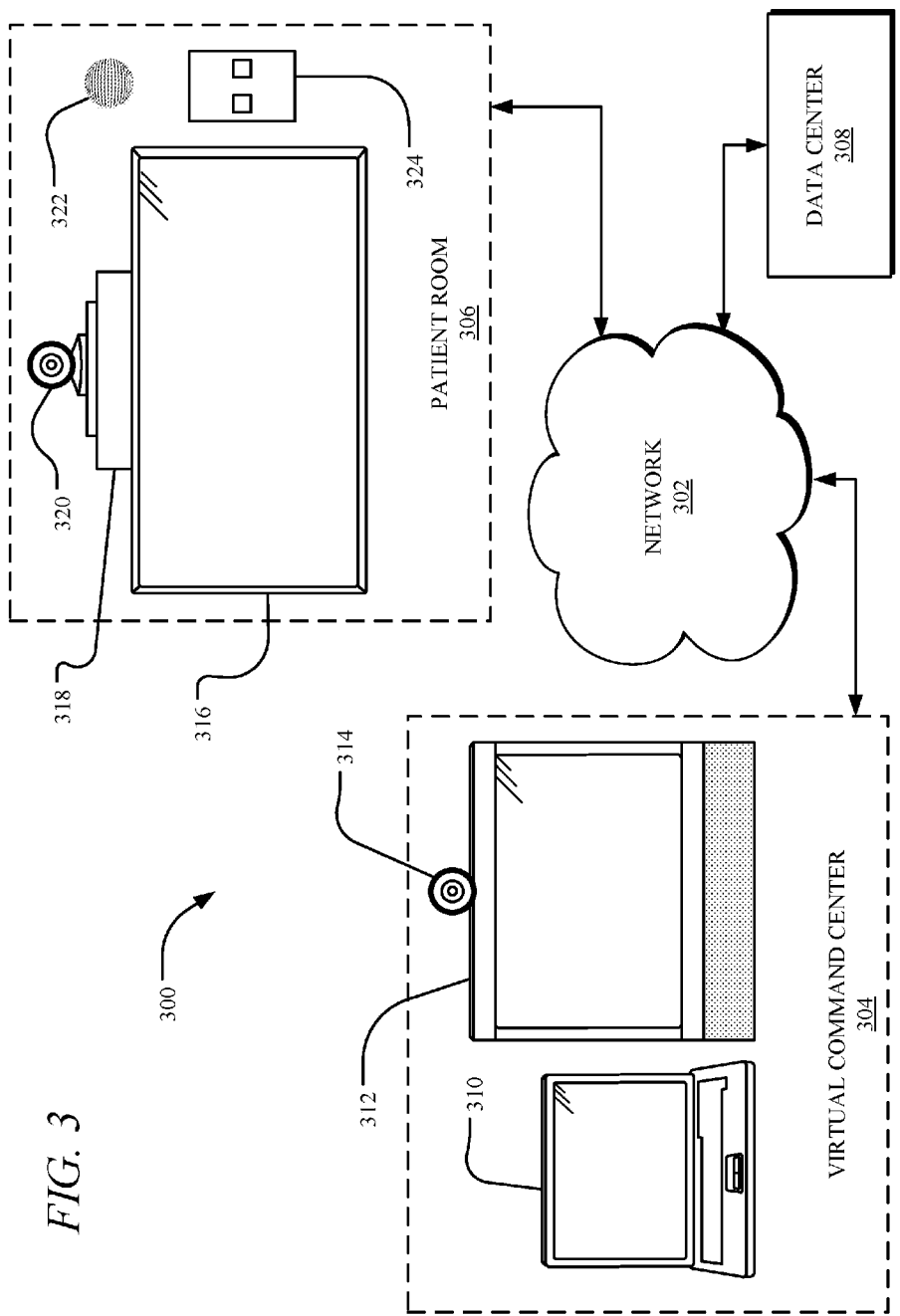
FIG. 3 depicts an example network environment for directing virtually integrated care delivery from a virtual command center to a patient room.

Referring to FIG. 3, an example network environment 300 for directing virtually integrated care delivery from a virtual command center 304 to a patient room 306 over a network 302 is depicted. A data center 308 facilitates the communication between the virtual command center 304 and the patient room 306, for example, as described with respect to FIG. 2.

In one implementation, the virtual command center 304 includes a computing device 310 in communication with a provider controller 312 having a camera 314 and microphone (not shown) for conferencing or sharing information with one or more team members over the network 302. Similarly, the patient room 306 includes a patient controller 318 in communication with a display 316, a camera 320, a microphone 322, and a call button 324 for conferencing or sharing information with one or more team members over the network 302. The computing device 310, the provider controller 312, and the patient controller 318 may be generally any form of computing device capable of interacting with the network 302, including, but not limited to, a personal computer, terminal, workstation, portable computer, mobile device, tablet, phone, pager, multimedia console, or other Internet Protocol (IP)-based telecommunication devices. The call button 324 may be, for example, a two-button controller configured to send a series of commands, such as place a call, when pressed. However, other forms of call buttons are contemplated. For example, the call button 324 may be presented on a touch-screen of a patient user device or a provider user device, which when pressed places a call associated with a patient room.

FIGS. 4-9 show example user interfaces generated by a computing device, such as a provider controller or a patient controller, and displayed in a window of a user device or other care delivery interface through which access to and interactions with the care delivery systems and methods described herein and related data are provided. It will be appreciated by those skilled in the art that such depictions are exemplary only and not intended to be limiting.

Figure 4:
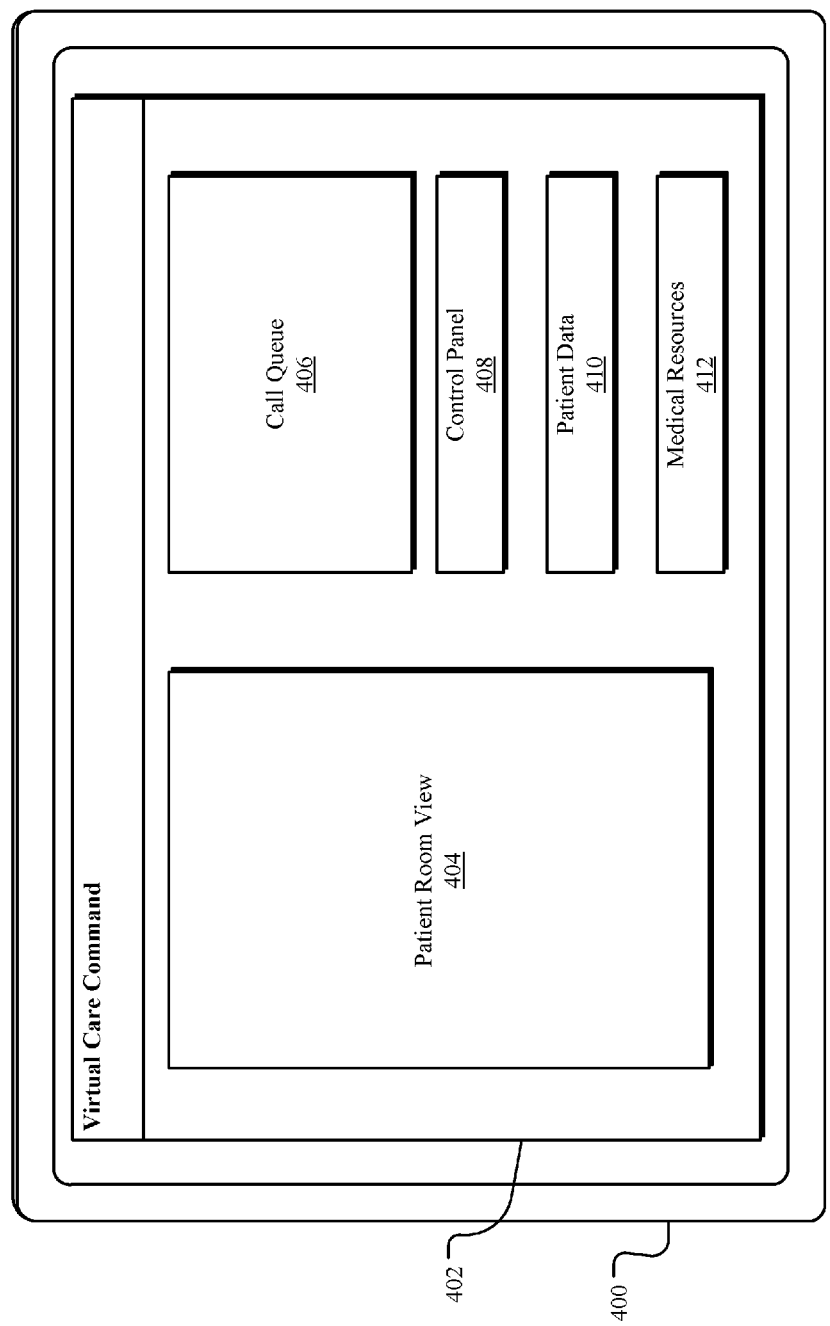
FIG. 4 shows an example virtual care command user interface.

Turning first to FIG. 4, an example virtual care command user interface 402 generated by and displayed with a computing device 400 is shown. In one implementation, the computing device 400 is a provider controller disposed in a virtual command center. However, other computing devices as described herein are contemplated.

In one implementation, the virtual care command user interface 402 includes a patient room view 404, a call queue 406, a control panel 408, patient data 410, and medical resources 412. The patient room view 404 provides real-time surveillance of one or more patient rooms. In one implementation, the patient room view 404 automatically switches between each of the patient rooms that are currently occupied. In another implementation, the patient room view 404 displays real-time surveillance of one or more selected patient rooms. For example, prior to initiating a care visit session with the patient 102, the virtual nurse 104 may use the patient room view 404 to view the room of the patient 102 to ensure that a physician visit, a medical procedure, patient rest, and/or the like is not interrupted. Additionally, the patient room view 404 may be used to monitor a status of one or more patients.

The call queue 406 provides a list of incoming calls (e.g., video and/or audio calls) from one or more patients and/or one or more providers. In one implementation, the call queue 406 distinguishes between calls originating from providers and calls originating from patients. For example, the call queue 406 may maintain a list of provider incoming calls separately from a list of patient incoming calls. In another example, the call queue 406 uses one or more indicators (e.g., visual color coding, labels, etc.) to distinguish provider calls from patient calls. The call queue 406 may further order the list(s) of incoming calls according to priority, as described herein. For example, a patient or provider may select an option when placing the call to elevate the priority level based on patient needs. Although the call queue 406 is discussed in the context of maintaining one or more lists of incoming calls, it will be appreciated that other forms of communications, including, without limitation, text messages, file or content exchanges, multimedia messages, and/or the like may be maintained in the call queue 406.

The control panel 408 includes one or more controls for navigating the virtual care command user interface 400 and other information, services, and resources, as well as for modifying one or more settings of the systems disclosed herein. In one implementation, the control panel 408 includes controls for: accessing a directory to select one or more parties (e.g., providers and/or patients) to which to send communications; modifying settings for those communications; sharing content with one or more parties (e.g., providers and/or patients), and/or the like.

The patient data 410 provides access to patient medical data for one or more patients for analysis, modification, input, and/or review. In one implementation, the patient data 410 includes patient charts, patient vitals, procedure results (e.g., medical imaging scans, lab work, medical tests, etc.) patient admission information, patient discharge information, patient tutorials or other education content, medications prescribed and/or administered, patient health history, and other information pertaining to the medical history and patient care. The patient data 410 may provide options for selecting one or more patients for which to obtain data or for acquiring anonymized data for a plurality of patients to view trends for a patient type, a provider, a provider team, a provider department, a procedure type, a patient condition type (e.g., a particular diagnosis), and/or the like.

The medical resources 412 provides access to a variety of medical resources pertaining to patient care. For example, the medical resources 412 may include peer-reviewed medical journals, textbooks, medical intelligence as described herein, publications, and/or the like.

Figure 5:
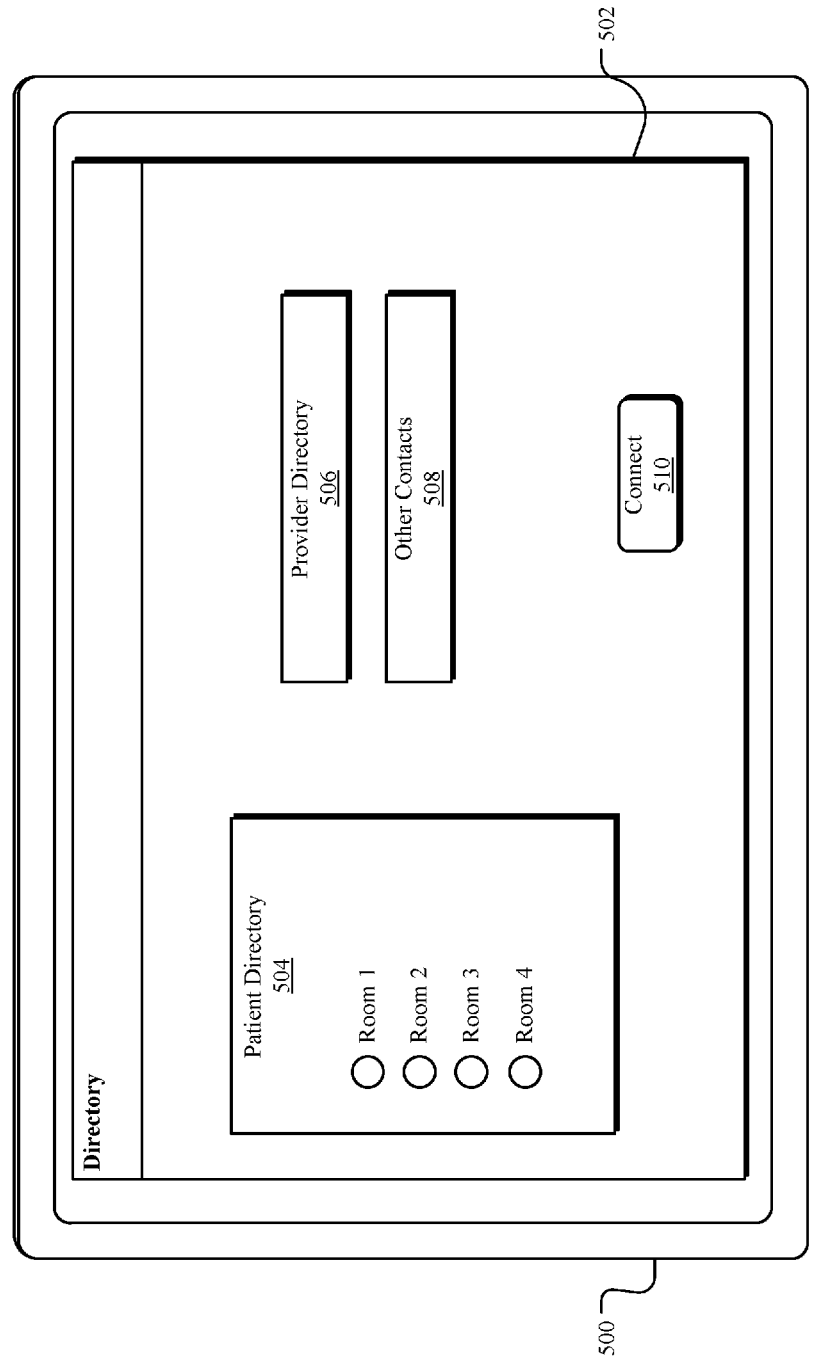
FIG. 5 shows an example directory user interface.

In one implementation, a directory option in the control panel 408 navigates to a directory user interface 502, which is displayed with a computing device 500, as shown in FIG. 5. In one implementation, the computing device 500 is a provider controller disposed in a virtual command center. However, other computing devices as described herein are contemplated.

The directory user interface 502 includes a patient directory 504, a provider directory 506, other contacts 508, and a connect button 510. In one implementation, the patient directory 504 lists one or more patient rooms configured to receive a communication. The one or more patient rooms included in the directory 504 may be limited to those rooms that are currently occupied by a patient or otherwise in use. In one implementation, a patient room listed in the directory 504 is selected and the connect button 510 is selected to connect with or otherwise send communications to the selected patient room. For example, the communication may include a care delivery communication to request a care visit session.

The provider directory 506 may similarly include one or more lists of providers, which may be selected to connect with or otherwise send communications. In one implementation, the provider directory 506 includes one or more lists of providers organized by care delivery team and/or by patient. For example, providers associated with the care of a patient or that will otherwise be included in provider rounds for that patient may be included in one list. Selection of this list may be used to send a round coordination communication to each of the providers to coordinate the providers for a visit to the patient during rounds. In one implementation, the round coordination communication is sent to the provider user devices as described herein.

The other contacts 508 may include a variety of other contacts associated with care delivery for one or more patients or other medical resources. For example, the other contacts 508 may include other virtual command centers, other hospitals or care facilities, pharmacies, various medical departments, primary caregivers, long term care facilities, and/or the like. The other contacts 508 may be organized by: patient, with contact information obtained during admission procedures or automatically from other intake procedures; location; contact type; and/or the like. The other contacts 508 may include options for adding or otherwise modifying contacts.

Figure 6:
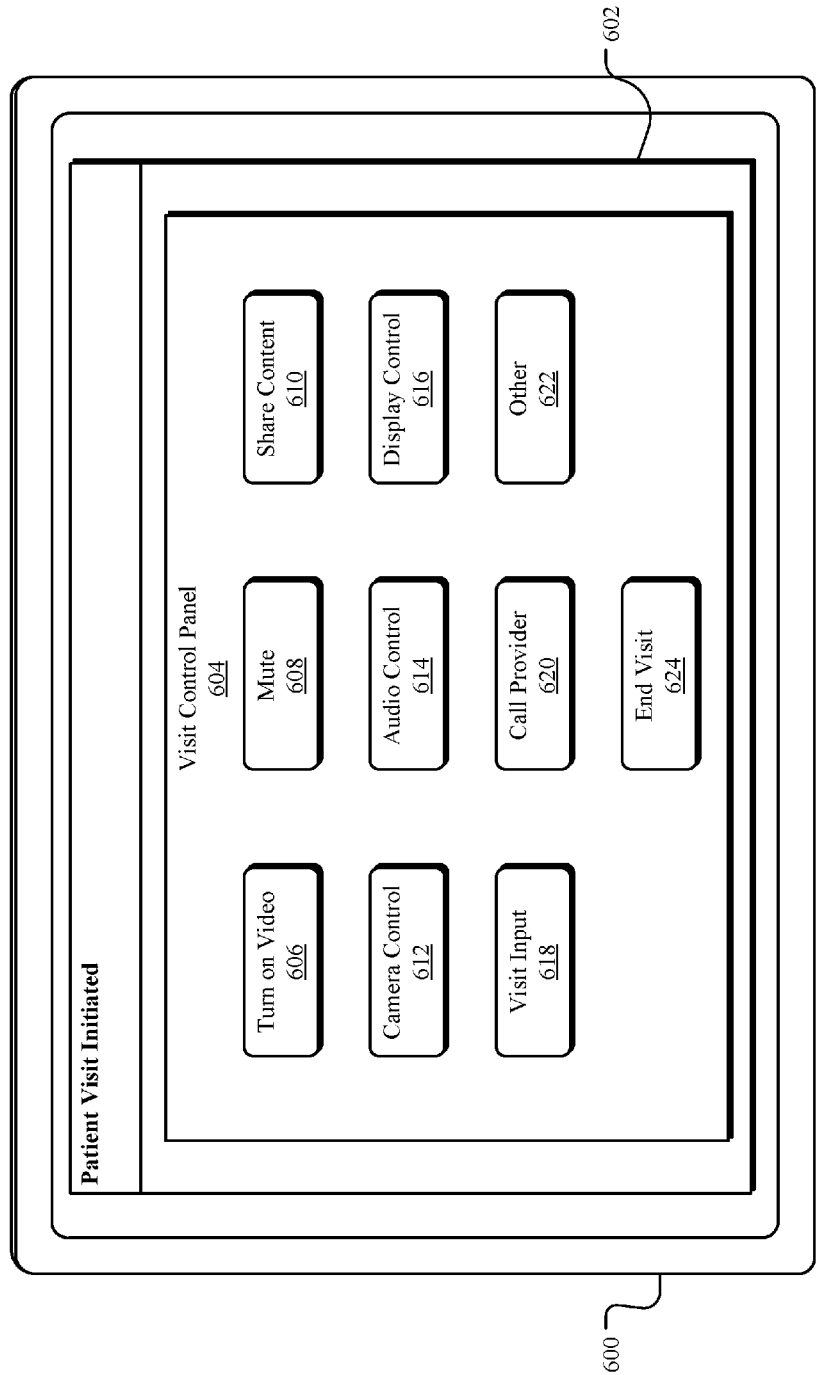
FIG. 6 shows an example patient visit user interface.

In one implementation, once patient room is selected from the patient directory 504 and the connect button 510 is selected, a care delivery communication is routed to the patient controller associated with the patient room selected. For patient privacy, among other considerations, the care delivery communication is delivered as an audio exclusive connection between the provider controller in the virtual command center and the patient controller. For example, as shown in FIG. 6, in one implementation, a patient visit user interface 602 may be displayed with a computing device 600 while permitting the exchange of audio communications between the virtual nurse 104 and the patient 102. In one implementation, the computing device 600 is a provider controller disposed in a virtual command center. However, other computing devices as described herein are contemplated.

In one implementation, the patient visit user interface 602 includes a visit control panel 604, including one or more controls (e.g., controls 606-624) for modifying settings for the connection and communication exchange between the provider controller and the patient controller. The audio exclusive connection may include a request for a care visit session. The request may be audio, text, graphical, and/or the like. The request for the care visit session may be accepted through a patient response, which may be audio, text, graphical, tactile, and/or the like. Upon acceptance of the request, a video connection between the patient controller and the provider controller may be delivered to initiate the care visit session. In one implementation, a turn on video option 606 may be used to establish the video connection.

Various controls may be used to modify the settings of the patient care delivery interface associated with the patient controller and/or the provider care delivery interface associated with the provider controller during the care visit session. For example, such controls may include, without limitation, a mute option 608, camera control 612, audio control 614, display control 616, and/or the like. The mute option 608 may be used to mute the audio on the provider side and/or the patient side. The audio control 614 permits the adjustment of sound volume through the speakers and/or microphones in the patient care delivery interface, as well as other controls to optimize sound delivery and/or capture. Further, the audio control 614 may be used to input or modify presets for the speakers and/or microphones.

The camera control 612 may be used to adjust one or more cameras in the patient room, for example, to change the image angle. In one implementation, once activated, the cameras in the patient room automatically identify and aim at the patient, for example, based on movement, object recognition, heat signature, and/or the like. Further, the camera control 612 may be used to input or modify presets for the cameras. The camera control 612 may include options for moving the cameras in a plurality of different directions (e.g., up, down, left, right, etc.). In one implementation, the camera control 612 includes near side controls and far side controls based on the positioning and number of cameras included in the patient care delivery interface.

The display control 616 may similarly be used to adjust one or more displays in the patient room, for example, to change the presentation angle relative to a position of the patient. In one implementation, the displays in the patient room automatically identify and orient towards the patient, for example, based on movement, object recognition, heat signature, and/or the like. Further, the display control 616 may be used to input or modify presets for the displays. The display control 616 may include options for moving the displays in a plurality of different directions (e.g., up, down, left, right, etc.), changing brightness, image size, and/or the like. Further, once a care visit session is initiated, the display control 616 may be used to select where to display content, including video of the virtual nurse 104, shared content, and/or the like. For example, the display control 616 may be used to select a display to present content and the location within the display to present the content.

The visit control panel 604 may further include options to share content 610, provide visit input 618, call provider 620, and other options 622. Using the share content option 610, shared content may be located and shared with the patient 102 via the patient care delivery interface. Shared content may include, without limitation, patient medical data, medical resources, medical intelligence, patient education and tutorials, checklists, and other applications, videos, and content. In one implementation, the shared content is presented in a manner permitting input and/or modification by both the virtual nurse 104 and the patient 102 simultaneously or otherwise collaboratively. The visit input 618 may be used to enter notes or save content relating to the care visit session or otherwise to care delivery for the patient 102. The call provider option 620 may be used to contact one or more of the providers associated with care for the patient, for example, to send a round coordination communication or other communication. An end visit option 624 may be used to end the care visit session or end the audio exclusive connection if the request for the care visit session is denied.

Figure 7:
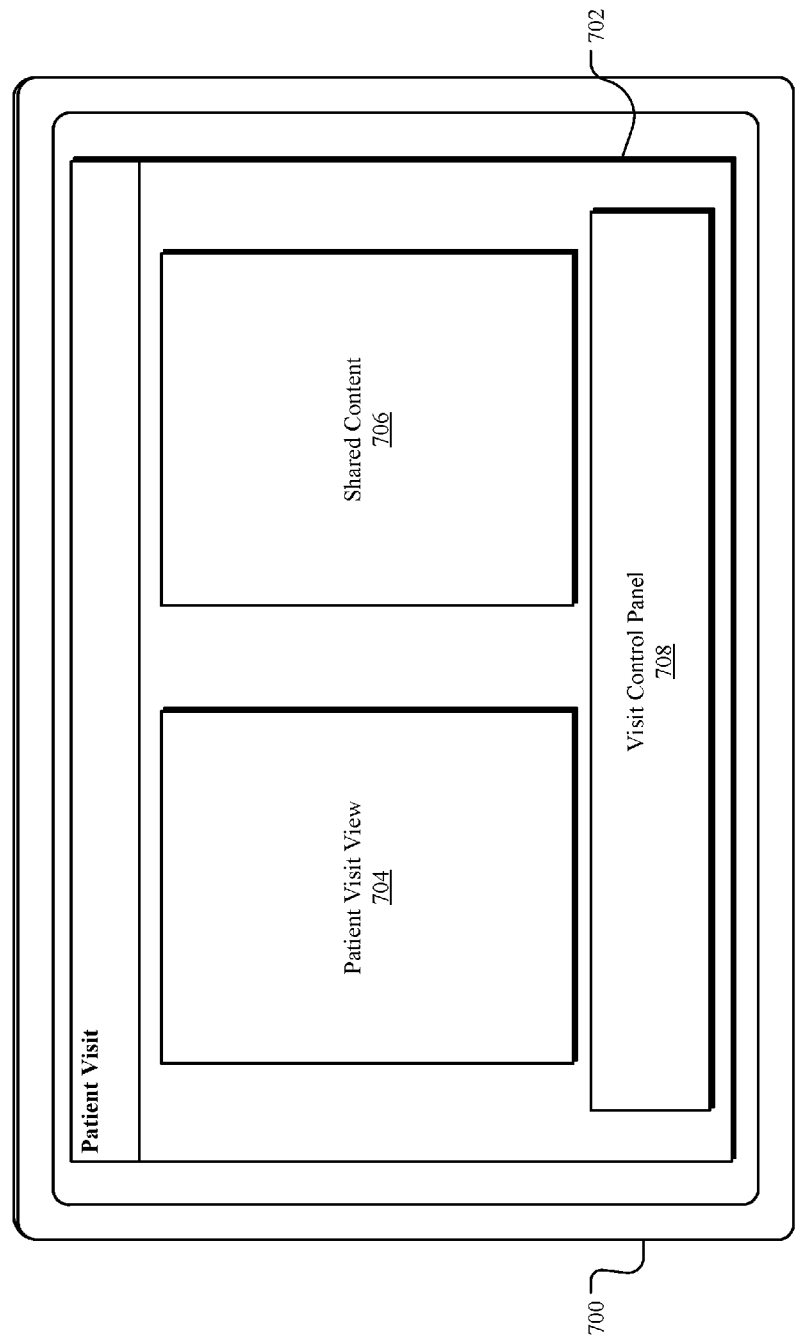
FIG. 7 shows an example provider care visit session user interface.

Turning to FIG. 7, in one implementation, once the request for the care visit session is approved and the video connection is established, a provider care visit session user interface 702 is presented with a computing device 700. In one implementation, the computing device 700 is a provider controller disposed in a virtual command center. However, other computing devices as described herein are contemplated.

In one implementation, the provider care visit session user interface 702 includes a patient visit view 704, shared content 706, and a visit control panel 708. The patient visit view 704 provides one or more real-time images, image sequences, or videos of the patient 102, and the shared content 706 presents any content that is selected for sharing with the patient 102, as discussed herein. The visit control panel 708 may include various controls substantially similar to the visit control panel 604 discussed above. In one implementation, the care visit session includes obtaining patient admission information, providing patient discharge information, or sharing patient medical data.

Figure 8:
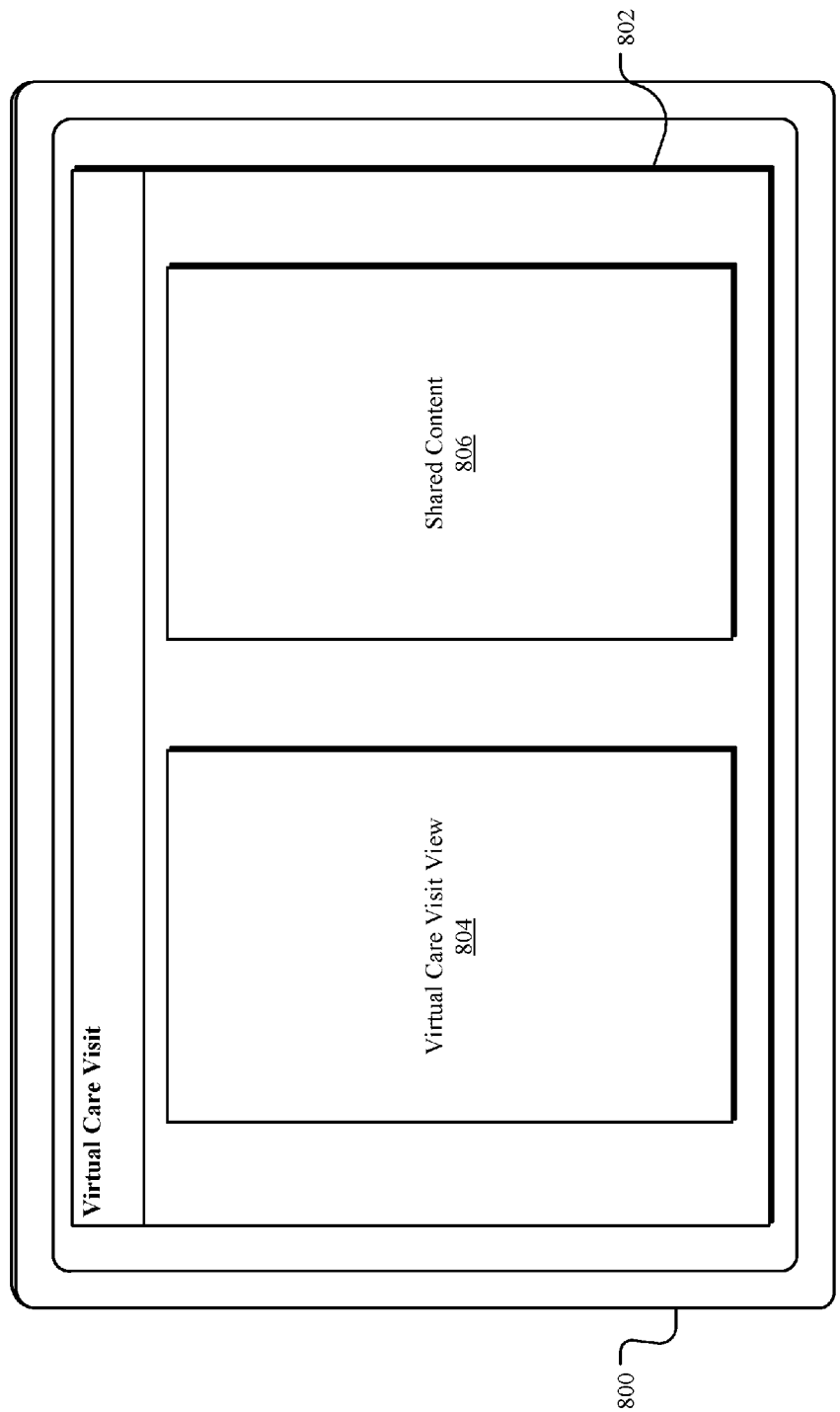
FIG. 8 shows an example patient care visit session user interface.

Similarly, as shown in FIG. 8, in one implementation, once the request for the care visit session is approved and the video connection is established, a patient care visit session user interface 802 is presented with a computing device 800. In one implementation, the computing device 800 is a patient controller associated with the patient room. However, other computing devices as described herein are contemplated.

In one implementation, the patient care visit session user interface 802 includes a virtual care visit view 804 and shared content 806. The virtual care view 804 provides one or more real-time images, image sequences, or videos of the virtual nurse 104, and the shared content 806 presents any content that is selected for sharing with the patient 102, as discussed herein. In one implementation, the location of the virtual care visit view 804 and the shared content 806 on one or more displays in the patient room are selected by the provider controller.

Figure 9:
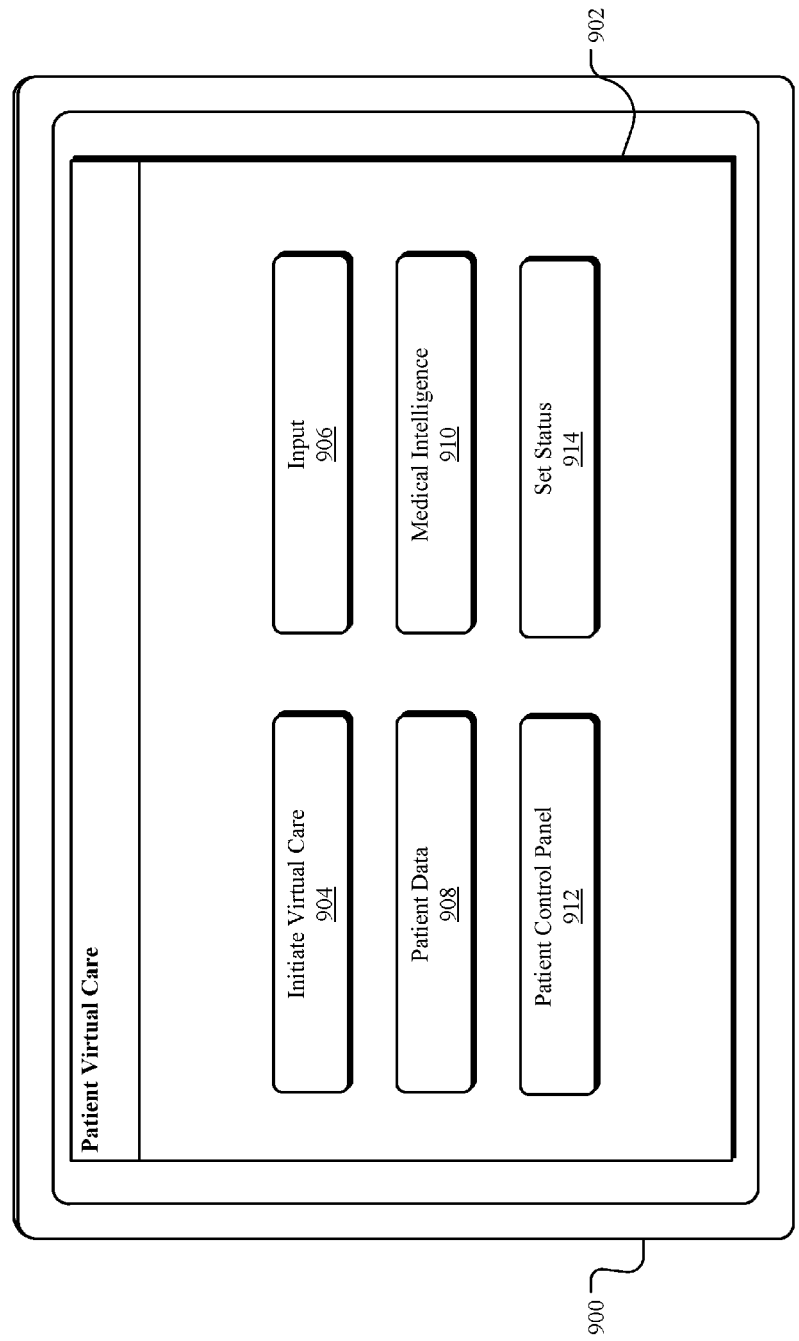
FIG. 9 shows an example patient virtual care user interface.

Turning to FIG. 9, in one implementation, when a visit care session is not occurring, a patient virtual care user interface 902 may be presented with a computing device 900. In one implementation, the computing device 900 is a patient controller associated with the patient room. However, other computing devices as described herein are contemplated.

In one implementation, the patient virtual care user interface 902 includes an initiate virtual care option 904, an input option 906, patient data 908, medical intelligence 910, patient control panel 912, and a set status option 914. The initiate virtual care option 904 may be used by the patient 102 or a provider to call the virtual nurse 104. In one implementation, the initiate virtual care option 904 may include options to select whether a provider is initiating the call or the patient 102. Once placed, the call is maintained in a queue until it can be answered, as described herein. Once connected, the patient care visit session user interface 802 may be presented.

The input option 906, the patient data 908, and the medical intelligence 910 may be used by the patient 102 to access, modify, and/or interact with various resources and content. The input option 906 changes the input source for the content on the displays. For example, the patient 102 may use the input option 906 to play television, music, stored content (e.g., a movie library), and/or care delivery content. The patient data 908 allows for searching and presentation of patient medical data, as described herein. The medical intelligence 910 permits access to medical intelligence and other medical resources, as described herein.

In one implementation, the patient virtual care user interface 902 further includes various controls, including the patient control panel 912, and the set status option 914. The patient control panel 912 permits the patient 102 to change the volume, channels, display settings, and/or the like. The set status option 914 may be used to request a care visit session, set a do not disturb status, and/or the like.

Figure 10:
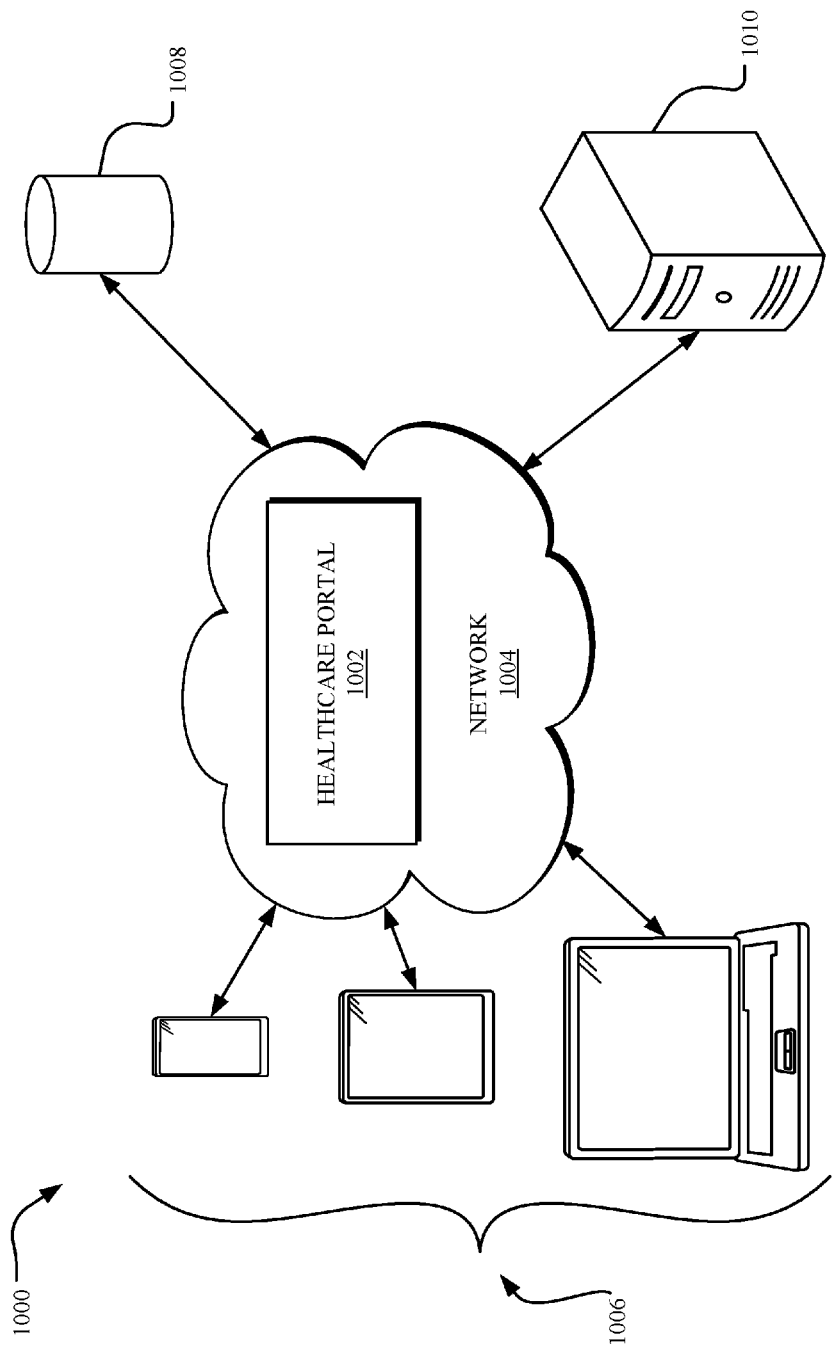
FIG. 10 illustrates an example network environment, including a healthcare portal running on a server or other computing device coupled with a network, for providing virtually integrated care delivery.

For a detailed description of an example network environment 1000 for providing virtually integrated care delivery, reference is made to FIG. 10. In one implementation, a user, such as a member of the interprofessional team, accesses and interacts with a healthcare portal 1002 using a user device 1006 to access or provide care delivery via a network 404 (e.g., the Internet).

The user device 1006 is generally any form of computing device capable of interacting with the network 1004, such as a personal computer, terminal, workstation, portable computer, mobile device, smartphone, tablet, multimedia console, etc. The network 1004 is used by one or more computing or data storage devices (e.g., one or more databases 1008 or other computing units described herein) for implementing the healthcare portal 1002 and other services, applications, or modules in the network environment 1000.

In one implementation, the network environment 1000 includes at least one server 1010 hosting a website or an application that the user may visit to access the healthcare portal 1002 and/or other network components. The server 1010 may be a single server, a plurality of servers with each such server being a physical server or a virtual machine, or a collection of both physical servers and virtual machines. In another implementation, a cloud hosts one or more components of the network environment 1000. The user devices 1006, the server 1010, and other resources connected to the network 1004 may access one or more other servers to access to one or more websites, applications, web services interfaces, storage devices, computing devices, or the like that are used for integrated healthcare delivery. The server 1010 may also host a search engine that the healthcare portal 1002 uses for accessing, searching for, and modifying patient data, team member data, education data, and other data. In one implementation, the healthcare portal 1002 provides access to the virtual nurse, members of the interprofessional team, data, and the like. The healthcare portal 1002 may be used for scheduling, performance tracking, and other care delivery services, as described herein.

Figure 11:
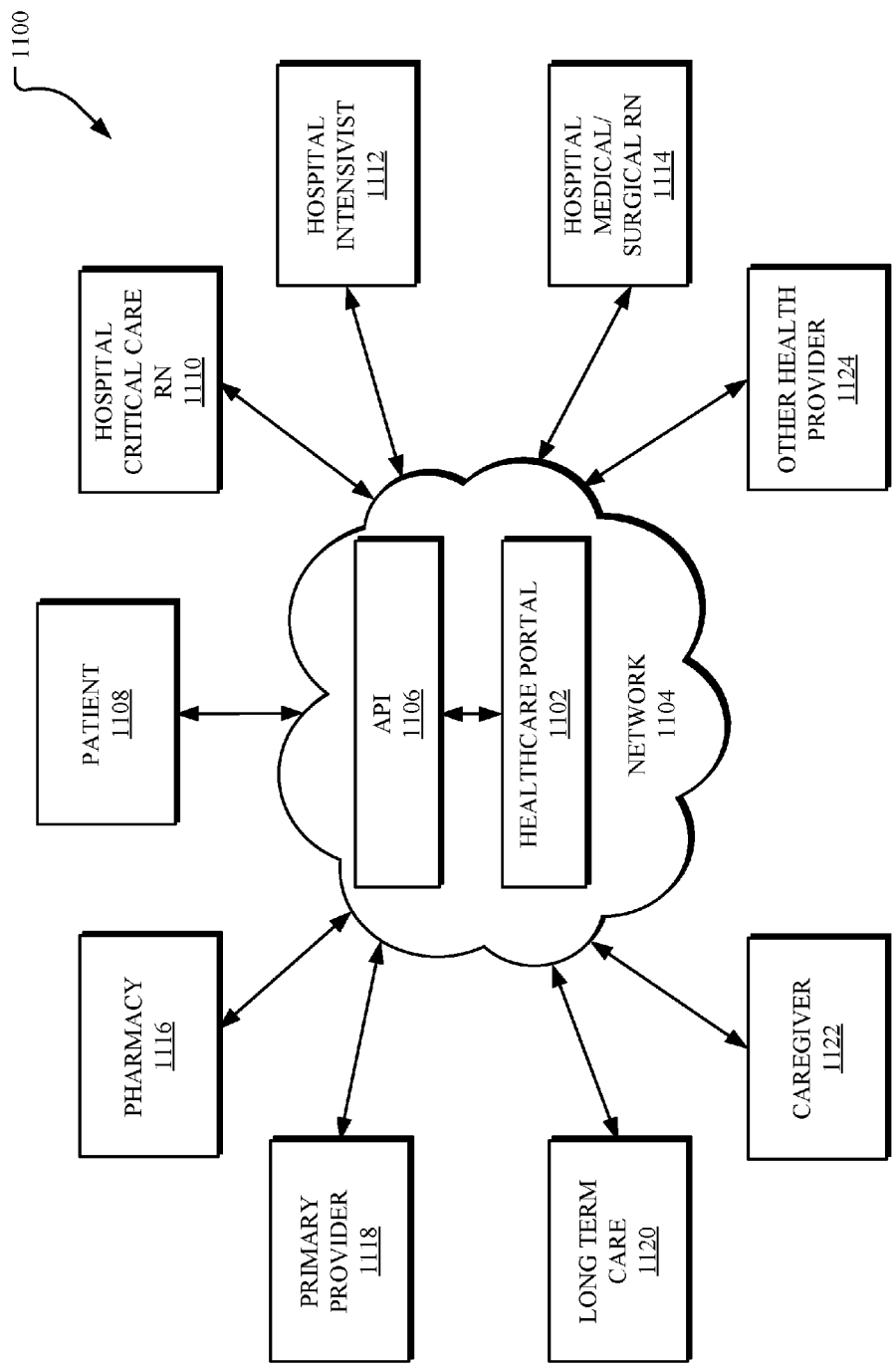
FIG. 11 illustrates an example network environment for a virtual care center.

Turning to FIG. 11, an example network environment 1100 for a virtual care center is shown. As shown in FIG. 11, various members of the interprofessional team may connect to each other and access patient or education data using the healthcare portal 1102 over a network 1104.

In one implementation, the team members may access and interact with the healthcare portal 1102, directly, for example, through a user device running a browser or other web-service that can interact with the network 1104. The user device is generally any form of computing device capable of interacting with the network 1104, as described herein. In another implementation, the team members may access and interact with the healthcare portal 1102 from software running on the user device utilizing an interface such as an application programming interface (API) 1106. Stated differently, the API 1106 can be called from an application or other software on the user device to pull or push data to and from the network 1104.

The team members may include various parties interested or authorized to participate in the care delivery of a patient 1108, including, without limitation, a hospital or critical care nurse 1110, a hospital intensivist 1112, a hospital medical or surgical nurse 1114, a pharmacist 1116, a primary care provider 1118, a long term care provider 1120, a caregiver 1122, or other health provider 1124. The network environment 1100 permits the team members to access and interact with each other and health information remotely.

Figure 12:
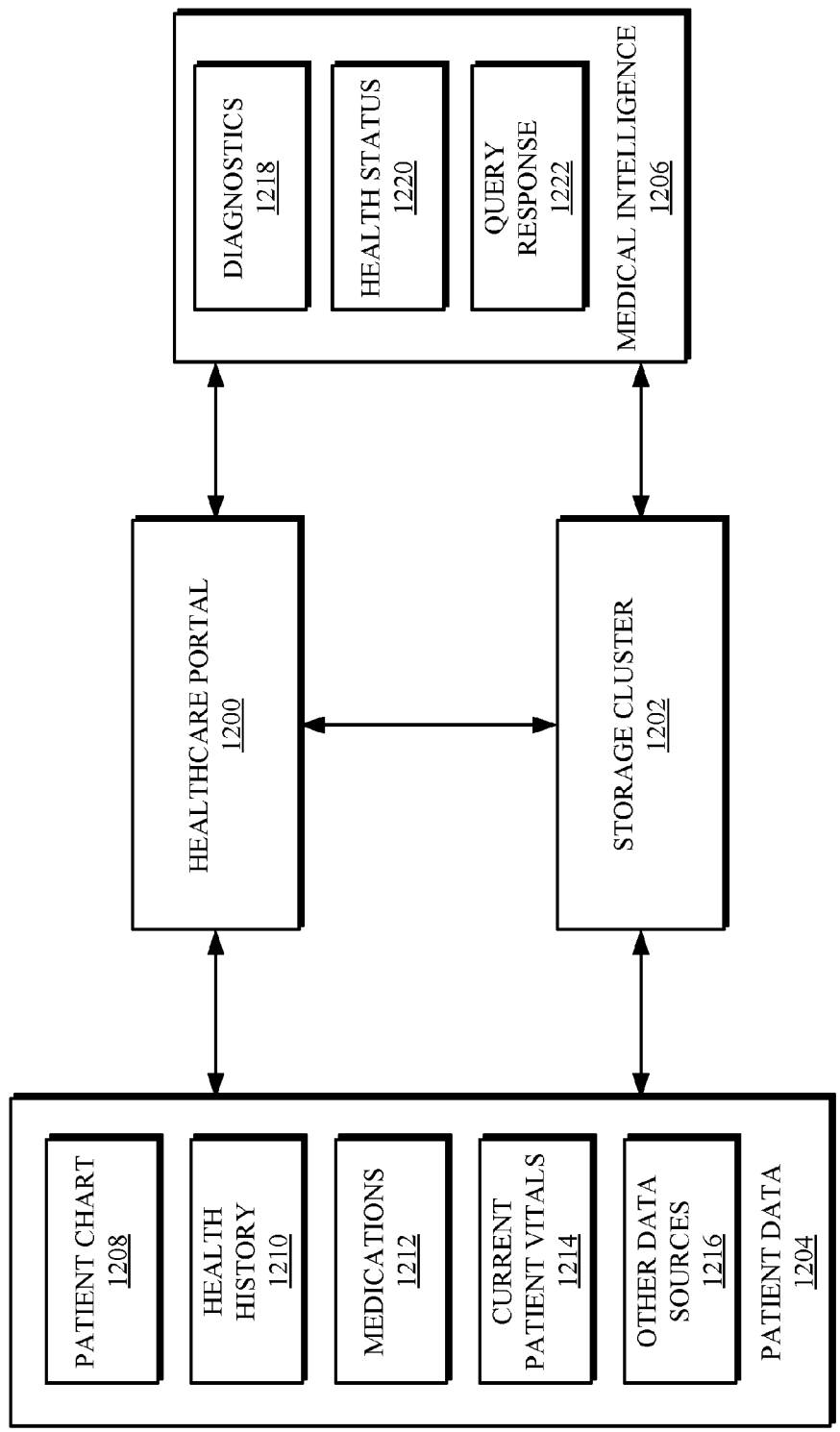
FIG. 12 shows an example system for generating medical intelligence based on patient data for use in care delivery.

As can be understood from FIG. 12, example system generates medical intelligence 1206 based on patient data 1204 for use in care delivery. In one implementation, a healthcare portal 1200, accessible to the team members over a network, is in communication with a storage cluster 1202 for retrieving the medical intelligence 1206.

In one implementation, the patient data 1204 includes data obtained from various data sources, including without limitation, a patient chart 1208, patient health history 610 (including patient health history and treatment and family health history), prescribed and current medications 1212, current patient vitals 1214 obtained via one or more medical devices, and other data sources 1216, such as textbooks, peer-reviewed journal articles, or combined, anonymized patient data for a plurality of patients.

The patient data 1204 is provided to the storage cluster 1202, which is configured to parse, tag, and/or associate data elements for storage and analysis. The storage cluster 1202 may include various modules, components, systems, infrastructures, and/or applications that may be combined in various ways, including into a single software application or multiple software applications. The patient data 1204 provided to the storage cluster 1202 is stored in one or more non-relational databases. The storage cluster 1202 is a distributed, scalable storage layer that is configured to store a large volume of structured and unstructured data. In one implementation, the storage cluster 1202 replicates and distributes blocks of data through cluster nodes, along with numerous other features and advantages. As such, the storage cluster 1202 generally manages the processing, storage, analysis, and retrieval of large volumes of data in a non-relational database.

The storage cluster 1202 serializes and stores the patient data 1204, such that the medical intelligence 1206 may be generated based on a query. The storage cluster 1202 processes a query in multiple parts at the cluster node level and aggregates the results to generate the network intelligence 1206. In one implementation, the storage cluster 1202 receives a query in structured query language (SQL), aggregates data stored in the storage cluster 1204, and outputs the medical intelligence 1206 in a format enabling further management, analysis, and/or merging with other data sources. The storage cluster 1202 may generate the medical intelligence 1206 using machine learning techniques, which generally refers to a machine learning through observing data that represents incomplete information about statistical happenings and generalizing such data to rules and/or algorithms that make predictions for future data, trends, and the like. Machine learning typically includes "classification" where machines learn to automatically recognize complex patterns and make intelligent predictions for a class. In one implementation, the medical intelligence 1206, includes patient diagnostics 1218, a health status of the patient 1220, and/or other query responses 1222.

Figure 13:
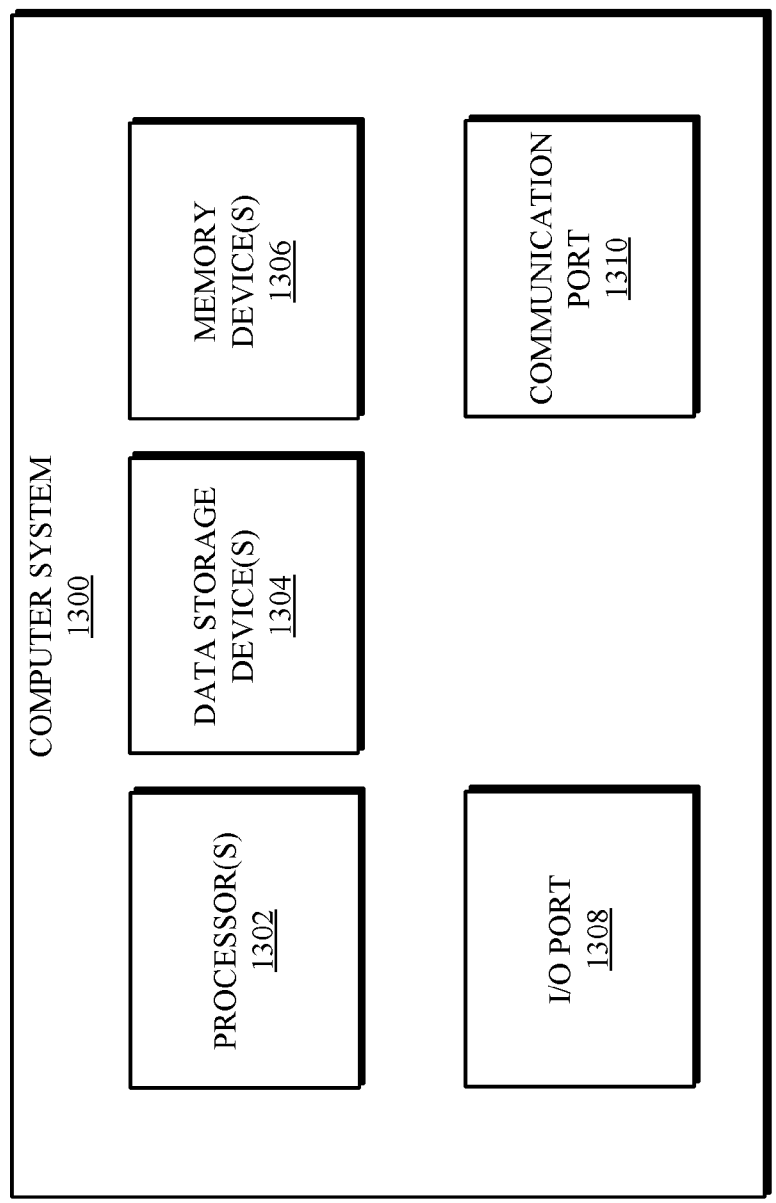
FIG. 13 is an example computing system that may implement various systems and methods discussed herein.

Referring to FIG. 13, a detailed description of an example computing system 1300 having one or more computing units that may implement various systems and methods discussed herein is provided. The computing system 1300 may be applicable to the patient controller, the provider controller, the patient user device, the provider user device, the care delivery interfaces, the communication manager device, the control center, and other computing or network devices. It will be appreciated that specific implementations of these devices may be of differing possible specific computing architectures not all of which are specifically discussed herein but will be understood by those of ordinary skill in the art.

The computer system 1300 may be a computing system is capable of executing a computer program product to execute a computer process. Data and program files may be input to the computer system 1300, which reads the files and executes the programs therein. Some of the elements of the computer system 1300 are shown in FIG. 13, including one or more hardware processors 1302, one or more data storage devices 1304, one or more memory devices 1308, and/or one or more ports 1308-1310. Additionally, other elements that will be recognized by those skilled in the art may be included in the computing system 1300 but are not explicitly depicted in FIG. 13 or discussed further herein. Various elements of the computer system 1300 may communicate with one another by way of one or more communication buses, point-to-point communication paths, or other communication means not explicitly depicted in FIG. 13.

The processor 1302 may include, for example, a central processing unit (CPU), a microprocessor, a microcontroller, a digital signal processor (DSP), and/or one or more internal levels of cache. There may be one or more processors 1302, such that the processor 1302 comprises a single central-processing unit, or a plurality of processing units capable of executing instructions and performing operations in parallel with each other, commonly referred to as a parallel processing environment.

The computer system 1300 may be a conventional computer, a distributed computer, or any other type of computer, such as one or more external computers made available via a cloud computing architecture. The presently described technology is optionally implemented in software stored on the data stored device(s) 1304, stored on the memory device(s) 1306, and/or communicated via one or more of the ports 1308-1310, thereby transforming the computer system 1300 in FIG. 13 to a special purpose machine for implementing the operations described herein. Examples of the computer system 1300 include personal computers, terminals, workstations, mobile phones, tablets, laptops, personal computers, multimedia consoles, gaming consoles, set top boxes, and the like.

The one or more data storage devices 1304 may include any non-volatile data storage device capable of storing data generated or employed within the computing system 1300, such as computer executable instructions for performing a computer process, which may include instructions of both application programs and an operating system (OS) that manages the various components of the computing system 1300. The data storage devices 1304 may include, without limitation, magnetic disk drives, optical disk drives, solid state drives (SSDs), flash drives, and the like. The data storage devices 1304 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1306 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1304 and/or the memory devices 1306, which may be referred to as machine-readable media. It will be appreciated that machine-readable media may include any tangible non-transistory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1300 includes one or more ports, such as an input/output (I/O) port 1308 and a communication port 1310, for communicating with other computing, network, or vehicle devices. It will be appreciated that the ports 1308-1310 may be combined or separate and that more or fewer ports may be included in the computer system 1300.

The I/O port 1308 may be connected to an I/O device, or other device, by which information is input to or output from the computing system 1300. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1300 via the I/O port 1308. Similarly, the output devices may convert electrical signals received from computing system 1300 via the I/O port 1308 into signals that may be sensed as output by a human, such as sound, light, and/or touch. The input device may be an alphanumeric input device, including alphanumeric and other keys for communicating information and/or command selections to the processor 1302 via the I/O port 1308. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 1300 via the I/O port 1308. For example, an electrical signal generated within the computing system 1300 may be converted to another type of signal, and/or vice-versa. In one implementation, the environment transducer devices sense characteristics or aspects of an environment local to or remote from the computing device 1300, such as, light, sound, temperature, pressure, magnetic field, electric field, chemical properties, physical movement, orientation, acceleration, gravity, and/or the like. Further, the environment transducer devices may generate signals to impose some effect on the environment either local to or remote from the example computing device 1300, such as, physical movement of some object (e.g., a mechanical actuator), heating or cooling of a substance, adding a chemical substance, and/or the like.

In one implementation, a communication port 1310 is connected to a network by way of which the computer system 1300 may receive network data useful in executing the methods and systems set out herein as well as transmitting information and network configuration changes determined thereby. Stated differently, the communication port 1310 connects the computer system 1300 to one or more communication interface devices configured to transmit and/or receive information between the computing system 1300 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1310 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1310 may communicate with an antenna or other link for electromagnetic signal transmission and/or reception.

In an example implementation, patient data, care delivery data, team member data, and software and other modules and services may be embodied by instructions stored on the data storage devices 1304 and/or the memory devices 1306 and executed by the processor 1302.

The system set forth in FIG. 13 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A method for virtually integrated health care delivery, the method comprising:

receiving a care delivery communication from a provider controller disposed in a virtual command center, the care delivery communication initiated through a selection of a patient room from a directory of patient rooms using the provider controller;

routing the care delivery communication over a network to a patient controller associated with the patient room using at least one communication manager device;

delivering the care delivery communication to the patient controller as an audio exclusive connection between the patient controller and the provider controller prior to an initiation of a care visit session, the audio exclusive connection including a request for the initiation of the care visit session, the request being acceptable by the patient controller through a patient response, the audio exclusive connection being terminated upon a denial of the request through the patient response; and upon acceptance of the request for the care visit session through the patient response, delivering a video connection between the patient controller and the provider controller, the delivery of the video connection initiating the care visit session.

2. The method of claim 1, wherein the care visit session includes obtaining patient admission information.

3. The method of claim 1, wherein the care visit session includes providing patient discharge information.

4. The method of claim 1, wherein the care visit session includes sharing patient medical data.

5. A system for virtually integrated health care delivery, the system comprising:

a patient controller disposed in a patient room;

a database storing a directory of patient rooms;

a provider controller disposed in a virtual command center and in communication with the patient controller over a network, the provider controller initiating a care delivery communication through a selection of the patient room from the directory of patient rooms; and a communication manager routing the care delivery communication over the network to the patient controller, the care delivery communication being delivered to the patient controller as an audio exclusive connection between the patient controller and the provider controller prior to an initiation of a care visit session, the audio exclusive connection including a request for the initiation of the care visit session, the request being acceptable by the patient controller through a patient response, the audio exclusive connection being terminated upon a denial of the request through the patient response, upon acceptance of the request for the care visit session through the patient response, a video connection between the patient controller and the provider controller being delivered, the delivery of the video connection initiating the care visit session.

6. The system of claim 5, wherein the care visit session includes obtaining patient admission information.

7. The system of claim 5, wherein the care visit session includes providing patient discharge information.

8. The system of claim 5, wherein the care visit session includes sharing patient medical data.

* * * * *